United States Patent [19]

Platel et al.

[11] Patent Number: 4,808,582
[45] Date of Patent: * Feb. 28, 1989

[54] NEW CINNAMOIC COMPOUNDS, THE PROCESS FOR PREPARING SAME AND THE USE THEREOF IN THERAPEUTICS

[75] Inventors: Alain Y. Platel, Puteaux; Guy R. Bourgery, Colombes; Patrick G. Guerret, Rueil Malmaison, all of France

[73] Assignee: Delalande S.A., Courbevoie, France

[*] Notice: The portion of the term of this patent subsequent to Jan. 27, 2004 has been disclaimed.

[21] Appl. No.: 28,092

[22] Filed: Mar. 19, 1987

Related U.S. Application Data

[63] Continuation of Ser. No. 654,250, Sep. 25, 1984, abandoned.

[30] Foreign Application Priority Data

Sep. 30, 1983 [FR] France ............... 83 15580

[51] Int. Cl.[4] .................. A61K 31/40; A61K 31/445; A61K 31/495; C07D 207/14; C07D 211/32; C07D 211/58; C07D 241/04; C07D 401/06
[52] U.S. Cl. .................. 514/212; 514/252; 514/253; 514/255; 514/299; 514/304; 514/316; 514/323; 514/329; 514/330; 514/331; 514/422; 514/423; 514/233.8; 514/235.2; 514/235.5; 544/349; 544/365; 544/372; 544/386; 544/391; 546/112; 546/125; 546/189; 546/191; 546/208; 546/210; 546/242; 546/244; 546/245; 548/300; 548/323; 548/452; 548/467; 548/512; 548/518; 548/526; 548/541; 548/557
[58] Field of Search ............... 544/349, 365, 372, 386; 544/391; 546/112, 125, 189, 191, 208, 210, 242, 244, 245; 548/300, 323, 452, 467, 512, 518, 526, 541, 557; 514/212, 234, 236, 237, 252, 253, 255, 299, 304, 316, 323, 329, 330, 331, 422, 423

[56] References Cited

U.S. PATENT DOCUMENTS

| | | | |
|---|---|---|---|
| 3,573,291 | 3/1971 | Fauran | 544/121 |
| 3,590,034 | 6/1971 | Fauran | 544/391 |
| 3,634,411 | 1/1972 | Fauran | 544/121 |
| 3,753,984 | 8/1973 | Fauran | 544/391 |
| 4,016,154 | 4/1977 | Turin | 544/372 |
| 4,029,650 | 6/1977 | Raynaud | 544/391 |
| 4,478,838 | 10/1984 | Itho | 544/386 |
| 4,639,452 | 1/1987 | Platel et al. | 544/365 |

FOREIGN PATENT DOCUMENTS 2520618 8/1983 France ............... 544/372

OTHER PUBLICATIONS

Hokuriku, Chemical Abstracts 99: 122498h (1983).
Kowa, Derwent Abstract 25240 E/13 (2/20/82).
Burger, "Medicinal Chemistry" 2nd Ed., p. 497, (1960).

Primary Examiner—Esther M. Kepplinger
Assistant Examiner—Robert Benson
Attorney, Agent, or Firm—Roylance, Abrams, Berdo & Goodman

[57] ABSTRACT

Compounds of formula:

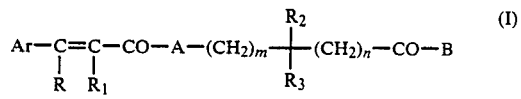

(I)

wherein: Ar is an aromatic group; R and $R_1$ are H or $CH_3$; A represents a nitrogenized heterocyclic radical; B is OH or forms with the adjacent CO group, either an amido group, or a carbonyloxy group; $R_2$ and $R_3$ are H or alkyl; m=0 or 1; and n=0, 1, 2 or 3.

These compounds are useful as drugs having stimulating, protecting and/or correcting activities of the cerebral functions.

16 Claims, No Drawings

NEW CINNAMOIC COMPOUNDS, THE PROCESS FOR PREPARING SAME AND THE USE THEREOF IN THERAPEUTICS

This is a continuation of application Ser. No. 654,250 filed Sept. 25, 1984, now abandoned.

The present invention relates to new cinnamoic compounds, the process for preparing same and the use thereof in therapeutics.

The compounds of the invention comprise more precisely:
the derivatives of the following general formula:

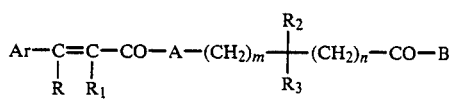

in which:

Ar represents a phenyl nucleus; a phenyl nucleus substituted by one or more halogen atoms, by one or more alkoxy groups with 1 to 4 carbon atoms or by one or more hydroxyl groups; a 1,3-benzodioxol

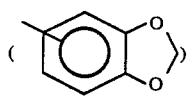

2,2-dimethyl-1,3-benzodioxol

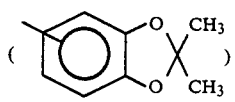

or 1,4-benzodioxanyl

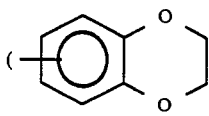

group); or a group with structure

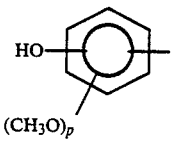

in which p has the value 1 or 2;

R and $R_1$ each represent a hydrogen atom or methyl group, R and $R_1$, however not representing a methyl group simultaneously;

CO-A— represents one of the following assemblies:

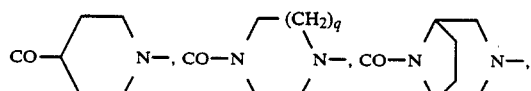

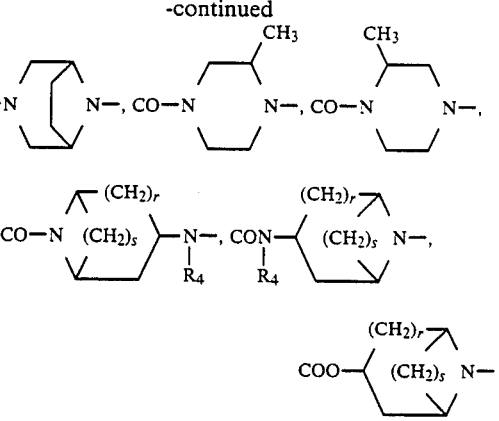

where q=1 or 2, $R_4$ represents the hydrogen atom or an alkyl group with 1 to 4 carbon atoms, s has the value 0, 2 or 3 and r has the value 0 or 1;

B represents a group chosen from the following: OH; $NH_2$; alkyloxy with 1 to 4 carbon atoms; benzyloxy; N-alkylamino or N,N-dialkylamino in which the alkyl residues have 1 to 4 carbon atoms; pyrrolidino; piperidino; morpholino; hexamethyleneimino; nortropanic

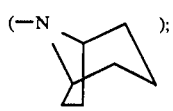

N-lactamic;

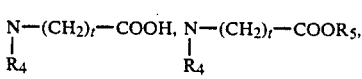

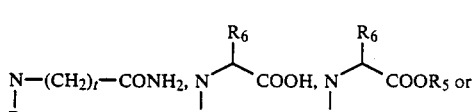

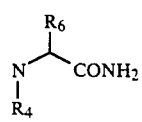

where t has the value 1, 2, 3 or 4, $R_4$ represents the hydrogen atom or an alkyl group with 1 to 4 carbon atoms, $R_5$ represents an alkyl group with 1 to 4 carbon atoms and $R_6$ represents an alkyl group with 1 to 4 carbon atoms or a benzyl or allyl group;

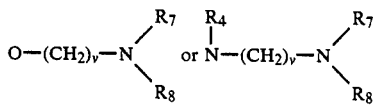

where v has the value 2 or 3 and

represents either a N,N-dialkylamino group in which the alkyl residues have 1 to 4 carbon atoms, or a pyrrolidino, piperidino, morpholino radical, $R_4$ having the same meanings as previously;

$R_2$ and $R_3$ each represent a hydrogen atom or alkyl group with 1 to 4 carbon atoms, $R_2$ and $R_3$ not however representing simultaneously an alkyl group comprising more than one carbon atom;

m has the value 0 or 1; and n has the value 0, 1, 2 or 3; including the enantiomers and diastereoisomers forms and the trans (E) and cis (Z) forms;

as well as the addition salts with organic or mineral acids or basis, the N-oxides, the quaternary ammoniums (especially the iodomethylates) and the hydrates of the above-mentioned derivatives (I);

B however not being able to represent:
* the OH, $NH_2$, alkyloxy with 1 to 4 carbon atoms, benzyloxy, N-alkylamino or N,N-dialkylamino group, in which the alkyl residues have 1 to 4 carbon atoms, or a pyrrolidino, piperidino, morpholino, hexamethyleneimino or nortropanic group, when

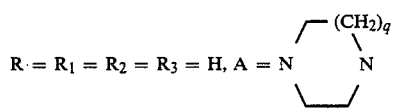

and m=n=0, and
* the $NH_2$, N-alkylamino or N,N-dialkylamino group in which the alkyl residues have 1 to 4 carbon atoms, or a pyrrolidino, piperidino, morpholino, or hexamethyleneimino group, when Ar represents the 2,3,4-trimethoxyphenyl or 3,4,5-trimethoxyphenyl group,

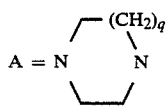

and the set $(R, R_1, R_2, R_3, m, n)=(H, H, CH_3, H, 0, O)$ or $(H, H, H, H, 1, O)$; and R and $R_1$ being able to represent only the hydrogen atom when CO—A— has the value

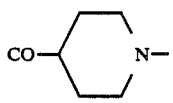

these restrictions concerning B, R and $R_1$ not however applying to the N-oxides and quaternary ammoniums mentioned above.

A/ The process according to the invention for preparing the derivatives (I) of the particular formula:

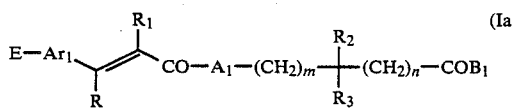

in which:

$Ar_1$ has the same meanings as Ar in (I), except for the cases where Ar represents a phenyl nucleus substituted by one or more hydroxyl groups or the group

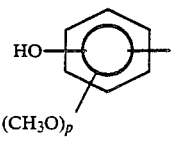

with p=1 or 2, $COA_1$— represents one of the following assemblies:

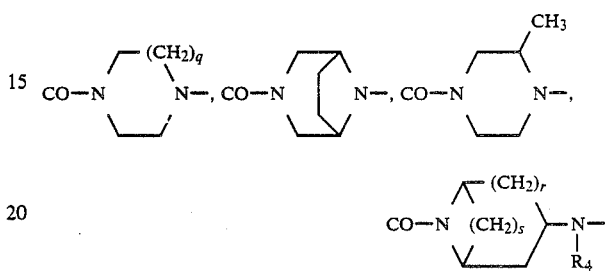

where q, r, s and $R_4$ have the same meanings as in I, $B_1$ has the same meanings as B in (I), except for the values: OH,

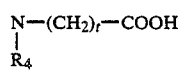

and

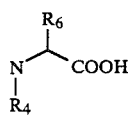

where t, $R_4$ and $R_6$ have the meanings as in (I),

R, $R_1$, $R_2$, $R_3$, m and n have the same meanings as in (I), consists in condensing the compounds of formula:

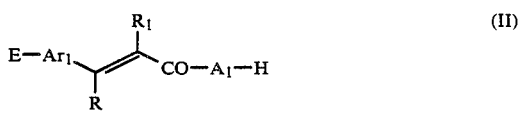

in which $Ar_1$, R, $R_1$ and $COA_1$— have the same meanings as in (Ia) with the compound of formula:

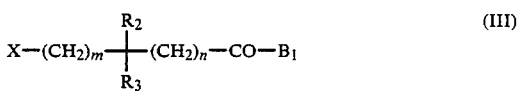

in which m, n, $R_2$, $R_3$ and $B_1$ have the same meanings as in (Ia) and X represents a good leaving group such as Cl for example. This condensation is preferably carrier out in an organic solvent as acetone, acetonitrile, methylethylketone, ethanol, ethyl acetate, D.M.F., T.H.F. or methylene chloride in the presence of an organic or mineral base, more particularly sodium or potassium carbonate.

B/ The process of the invention for preparing the derivatives (I) of the particular formula:

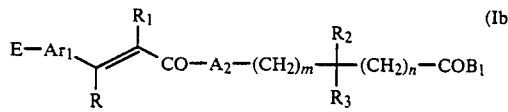  (Ib)

in which $Ar_1$, R, $R_1$, $R_2$, $R_3$, $B_1$, m and n have the same meanings as in (Ia) and $COA_2$— represents one of the following assemblies:

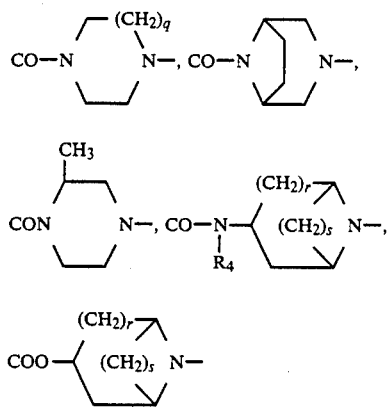

where q, r, s and $R_4$ have the same meanings as in (I) consists: 1—either in condensing, in accordance with the so-called "BOISSONNAS" reaction, in the presence of an organic basic (preferably triethylamine) and an alkyl chloroformate such as ethyl or isobutyl chloroformate, in an aprotic solvent (such as chloroform, methylene chloride, DMF or THF) the acids of formula:

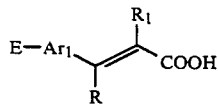  (IV)

in which $Ar_1$, R and $R_1$ have the same meanings as in (Ib) with the derivatives of formula:

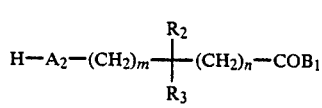  (V)

in which $A_2$, $B_1$, $R_2$, $R_3$, m and n have the same meanings as in (Ib),

2—or in condensing the acids (IV) with the derivatives (V) in the presence of N-hydroxybenzotriazole, D.C.C.I. and a base such as triethylamine in an aprotic organic solvent such as THF, 3—or in condensing the acid chlorides of the acids (IV) (chlorides obtained for example by action of thionyl chloride on the acids (IV) according to conventional methods) with the compounds (V) in an aprotic medium such as toluene or methylene chloride in the presence of a base such as triethylamine.

C/ The process of the invention for preparing the derivatives (I) of the particular formula:

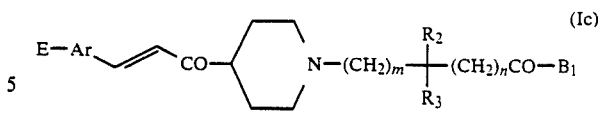  (Ic)

in which Ar, $R_2$, $R_3$, m and n have the same meanings as in (I) and $B_1$ has the same meanings as in (Ia), consists in condensing in an alcohol medium, in the presence of a base such as NaOH, the aldehydes of formula:

$$Ar-CHO \quad (VI)$$

in which Ar has the same meanings as in (I) with the derivatives of formula:

  (VII)

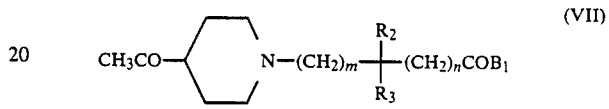

in which $R_2$, $R_3$, B, m and n have the same meanings as in (Ic), this condensation being followed by an acid treatment when, in (Ic), Ar represents a substituted phenyl nucleus having at least one hydroxyl group or the group

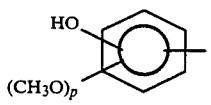

(with p = 1, 2).

D/ The process of the invention for preparing trans derivatives (I) in which B represents the group OH or a chain $$\overset{R_4}{\underset{|}{N}}-(CH_2)_t-COOH$$

or

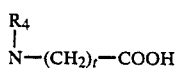

in which t, $R_4$ and $R_6$ have the same values as in (I), consists in hydrolysing the ester group of the derivatives (I) of the particular formula:

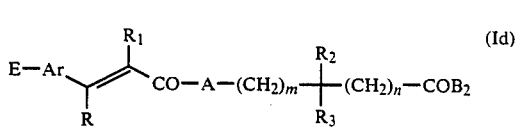  (Id)

in which Ar, R, $R_1$, $R_2$, $R_3$, A, m and n have the same meanings as in (I) and —$B_2$ represents a group

, $$-\underset{\underset{R_4}{|}}{N}-(CH_2)_t-COO-\Big|$$

or $$-\underset{\underset{R_4}{|}}{N}\overset{R_6}{\underset{|}{\diagdown}}COO-\Big|$$

where t, $R_4$ and $R_6$ have the same meanings as in (I). This hydrolysis is preferably carried out with hydrochloric acid diluted in acetic acid or with trifluoroacetic acid in an organic solvent such as methylene chloride.

E/ The process of the invention for preparing the trans derivatives (I) for which Ar designates a phenyl nucleus substituted by one or more hydroxyl groups or the group

[structure: phenyl ring with HO and $(CH_3O)_p$ substituents]

(with p=1 or 2), consists in treating, by means of ammonia in a methanol medium, the mixed carbonates of formula:

$$E-\underset{(CH_3O)_y}{\overset{(R_9OCOO)_x}{\diagup\!\!\!\!\!\bigcirc\!\!\!\!\!\diagdown}}\overset{R_1}{\underset{\underset{O}{\overset{|}{C}}}{\overset{|}{C}}}A_3\text{---}(CH_2)_{\overline{m}}\overset{R_2}{\underset{R_3}{\overset{|}{C}}}(CH_2)_{\overline{n}}\text{---}COB_1 \quad (VIII)$$

in which $R_9$ represents an alkyl group with 1 to 4 carbon atoms, x has the value 1 or 2, y has the value 0, 1 or 2 (with the restriction that x has the value 2 only when y=0), R, $R_1$, $R_2$, $R_3$, m and n have the same meanings as in (I), $B_1$ has the same meanings as in (Ia) with CO—$A_3$— has the same meanings as CO—A— in (I), except for the value

[structure: CO—piperidine—N—]

F/ The process of the invention for preparing the derivatives (I) of the particular formula:

$$E-Ar_1\overset{R_1}{\underset{R}{\diagdown\!\!\!\!\!=\!\!\!\!\!\diagup}}CO-A-(CH_2)_m\overset{R_2}{\underset{R_3}{\overset{|}{\!\!\!\!-\!\!\!\!\!}}}(CH_2)_n-COB_3 \quad (Ie)$$

in which $Ar_1$, R, $R_1$, $R_2$, $R_3$, m and n have the same meanings as in (Ia), A has the same meanings as in (I) and $B_3$ represents an N-alkylamino or N,N-dialkylamino group whose alkyl residues have 1 to 4 carbon atoms, a pyrrolidino, piperidino, morpholino, hexamethyleneimino or nortropanyl group or the groups $$\underset{\underset{R_4}{|}}{N}-(CH_2)_t-CONH_2, \quad \underset{\underset{R_4}{|}}{N}-(CH_2)_t-COOR_5,$$

$$\underset{\underset{R_4}{|}}{N}\overset{R_6}{\underset{|}{\diagdown}}CONH_2, \quad \underset{\underset{R_4}{|}}{N}\overset{R_6}{\underset{|}{\diagdown}}COOR_5,$$

in which t, $R_4$, $R_5$ and $R_6$ have the same meanings as in (I), consists in condensing in accordance with the operating method described in paragraph B/2-, the acids of formula:

$$E-Ar_1\overset{R_1}{\underset{R}{\diagdown\!\!\!\!\!=\!\!\!\!\!\diagup}}CO-A-(CH_2)_m\overset{R_2}{\underset{R_3}{\overset{|}{\!\!\!\!-\!\!\!\!\!}}}(CH_2)_n-COOH \quad (If)$$

in which $Ar_1$, R, $R_1$, $R_2$, $R_3$, A, m and n have the same meanings as in (Ie) with the amines of formula:

$$H-B_3 \quad (XV)$$

in which $B_3$ has the same meanings as in (Ie), the compounds (If) being obtained by the method described in paragraph D/.

G/ The process of the invention for preparing the derivatives (I) for which the chain $$\underset{R\ R_1}{\overset{\diagup\!\!\!\!\!=\!\!\!\!\!\diagdown}{}}CO-$$

is cis (Z), consists in a photochemical isomerisation of the corresponding trans (E) derivatives according to the method described in French Pat. No. 82 03045.

H/ The derivatives (I) of the present invention may be salified by the usual methods. The salification may for example be obtained by action on these derivatives of a mineral acid such as hydrochloric acid or an organic acid such as maleic acid, this operation being preferably carried out in a solvent or a mixture of solvents such as acetone, ethanol or water or else by addition of an organic or mineral base under the same conditions.

I/ The N-oxides of the invention are prepared by the usual methods preferably by action of organic peracids (such as M.C.P.B.A. or para-nitroperbenzoic acid) in an aprotic solvent such as methylene chloride preferably, on the derivatives (I) of the invention.

J/ The quaternary ammoniums of the derivatives (I) of the invention and especially the iodomethylates are prepared by action of alkyl chloride preferably methyl iodide, on the derivatives (I) in solution in an organic solvent by the usual methods.

K/ The enantiomers of the derivatives (I) of the invention are obtained either by conventional resolution methods, from salts of the derivatives (I) [salts obtained by action of an optically active organic acid on derivatives (I)], or by stereospecific synthesis by the methods described in the preceding paragraphs A/, B/, C/, but with the optically active compounds (III), (V) and (VII).

The disastereoisomers are obtained in the form of diastereoisomers pairs, by chromatography on a silica or alumina column.

The compounds (II) for which COA$_1$— represents the group

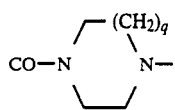

in which q=1 or 2 are obtained by condensation of piperazine or homopiperazine with the acid chlorides of the acids of formula (IV).

The compounds (II) for which COA$_1$— represents the group

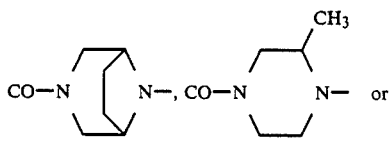

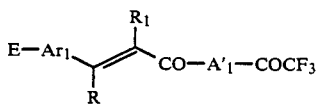

are obtained by basic hydrolysis of the compounds of formula:

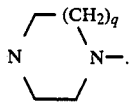      (IIa)

in which Ar$_1$, R and R$_1$ have the same meanings as in (II) and COA'$_1$— has the same meanings as COA$_1$— in (II), except for the value

The compounds (IIa) are themselves obtained by condensation, by one or other of the methods described in the above paragraph B/, of the acids (IV) with the derivatives of formula:

H—A'$_1$—COCF$_3$      (IX)

in which A'$_1$— has the same meanings as in (IIa).

The compounds (IX) are obtained by catalytic hydrogenolysis (preferably with palladium on charcoal) of the compounds of formula:

R$_{10}$—A'$_1$—COCF$_3$      (X)

in which R$_{10}$ represents a benzyl or benzyloxycarbonyl group and A'$_1$ has the same meanings as in (IIa), the compounds (X) being obtained by action of trifluoroacetic anhydride on the compounds of formula:

R$_{10}$—A'$_1$—H      (XI)

in which R$_{10}$ and A'$_1$ have the same meanings as in (X).

The compounds (III) of the particular formula:

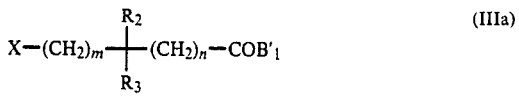      (IIIa)

in which B'$_1$ represents an amino, N-alkylamino or N,N-dialkylamino group whose alkyl residues have 1 to 4 carbon atoms, or a pyrrolidino, piperidino, morpholino, hexamethyleneamino, nortropanic, N-lactamic,

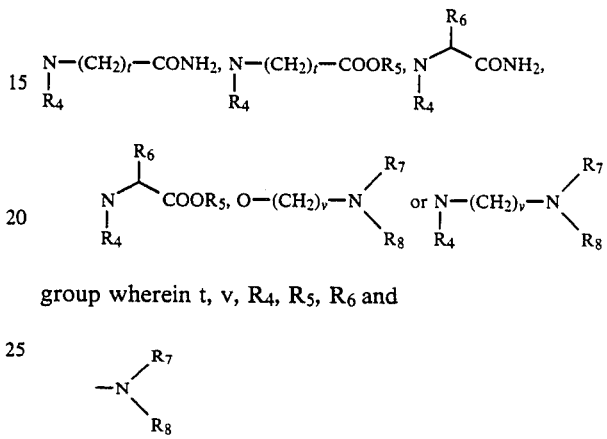

group wherein t, v, R$_4$, R$_5$, R$_6$ and

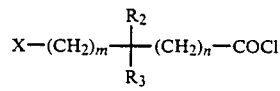

have the same meanings
as in (I) and X, R$_2$, R$_3$, m and n have the same meanings as in (III) are obtained by condensation of the compounds:

      (XII)

in which X, R$_2$, R$_3$, m and n have the same meanings as in (III), with the compounds of formula:

HB'$_1$      (XIII)

in which B' has the same meanings as in (IIIa).

These condensations are carried out in the presence of an organic base, such as triethylamine preferably, and in aprotic solvents such as toluene, methylene chloride or THF for preference.

The compounds (XIII) for which B'$_1$ represents the groups

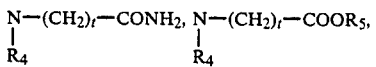

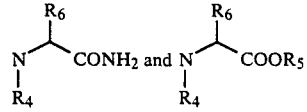

in which t, R$_4$, R$_5$ and R$_6$ have the same meanings as in (I) are obtained by the conventional methods described in the litterature and particularly the methods described in J. Chem. Soc. 1965, 7305.

The compounds (V) for which HA$_2$— represents the group

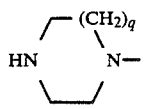

or

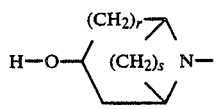

in which q, r and s have the same meanings as in (I) are obtained by condensation preferably in 96 ethanol, of the compounds of formula (III) respectively with piperazine, homopiperazine or the hydroxylated derivatives of formula

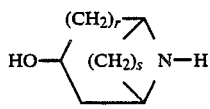

in which r and s have the same meanings as in (I).

The compounds (V) of the particular formula:

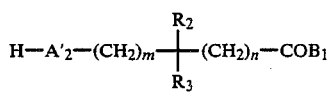

in which H—A'$_2$— represents the group

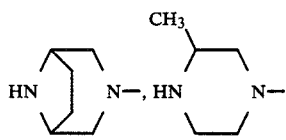

or

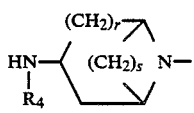

in which R$_4$, r and s have the same meanings as in (I) are obtained by basic hydrolysis of the compounds of formula:

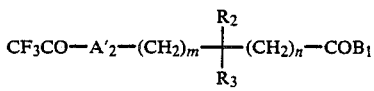

in which A'$_2$, R$_2$, R$_3$, B$_1$, m and n have the same meanings as in (Va).

The compounds (XIV) are obtained by condensation of the compounds of formula (III) with the compounds of formula (IX).

The compounds (VII) are obtained by condensation of the compound of formula:

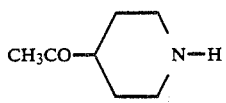

on the compounds (III), this condensation being carried out by the method of process A/ above.

Finally, the compounds (VIII) are obtained by the so-called "BOISSONNAS" reaction using the method described in paragraph B/1- between the acids of formula:

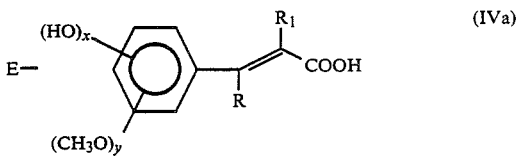

in which R and R$_1$, x and y have the same meanings as in (VIII), either with the compounds (V) or with the compounds (IX), but doubling the amounts of alkyl chloroformate and triethylamine used. In the case of condensation of compounds (IVa) with compounds (IX), the reaction is then followed by a basic treatment (K$_2$CO$_3$ in methanol) and condensation, by the method described in paragraph A/ above, of the compounds (III) on the compounds obtained by formula:

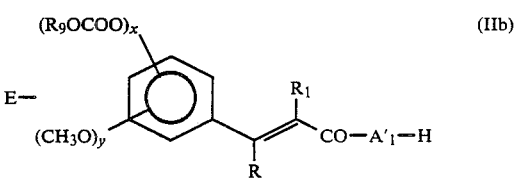

in which R$_9$, x, y, R and R$_1$ have the same meanings as in (VIII) and A'$_1$, has the same meanings as in (IIa).

The following preparations are given by way of non limitative examples to illustrate the invention.

EXAMPLE 1

E-1-(3,4-dioxymethylene cinnamoyl) 4-(2-pyrrolidino carbonyl ethyl) piperazine hydrochloride [(I), code number 2]

A suspension of 10.8 g of E-3,4-dioxymethylene cinnamoyl piperazine (II), 8.7 g of 1-chloro-2-pyrrolidinocarbonyl ethyl (III) and 5.8 g of potassium carbonate in 50 ml of ethanol is heated to reflux for 10 hours. Then it is filtered, the filtrate is evaporated, the residue is taken up in methyl ethyl ketone, washed with water, dried on sodium (or magnesium) sulfate, filtered, the filtrate is evaporated and the residue crystallized in isopropylic ether. The product obtained is dissolved in ethanol; hydrochloric ethanol is added and the precipitate obtained is filtered. Thus 8.5 g of the expected product are obtained, of which the physical and analytical data are given in table I below.

By the same process, but from the corresponding reagents compounds are obtained shown in table I under code numbers 3, 4, 6, to 10, 17, 19, 20, 24, 29 to 31, 33, 35, 38, 40, 44 to 47, 49 to 54, 57 to 59, 63, 64, 68 and 69, as well as the compounds (V) for which H—A$_2$— represents the group

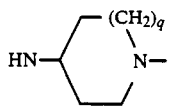

or

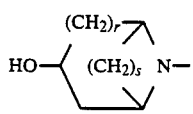

and the compounds (XIV), (VII) and (VIII) (from the compounds IIb).

EXAMPLE 2 tertiobutyl E-N-4-[2-[1-(4-methoxy-3-isobutyloxycarbonyloxy cinnamoyl) 4-piperazino]acetamido]butanoate (VIII)

To a solution of 5 g of E-3-hydroxy 4-methoxy cinnamic acid (IVa) in 50 ml of THF are added 5.3 g of triethylamine, then the solution is cooled to $-10°$ C. and 7 g of isobutyl chloroformate are added in 20 minutes. It is left under agitation for 15 minutes then a solution of 7.4 g of tertiobutyl N-4-[2-(N-piperazino)acetamido]butanoate (V) are introduced in 40 minutes. They are left in contact for 15 minutes, then filtered, the filtrate is evaporated, the residue is taken up in ethyl acetate, washed in water, then with a dilute aqueous solution of sodium carbonate, then with water, dried on sodium or magnesium sulfate, filtered, the filtrate is evaporated and the residue crystallized in isopropylic ether. 10.9 g of the expected product are obtained (Yield: 75%).

Melting point: 80° C.
Empirical formula: $C_{29}H_{43}N_3O_8$
Molecular weight: 561.66

By the same process, but from the corresponding reagents, the compounds shown in table I under the code numbers 2 to 4, 6, 8 to 10, 17, 19, 20, 22, 23, 29 to 31, 33, 35, 38, 40, 49 to 54, 58, 59, 61, 65 and 66 are obtained, as well as the compounds of formula (IIa).

EXAMPLE 3

E-1-(3,4-dioxymethylene cinnamoyl 4-[(4-pyrrolidino carbonyl)butyl]piperazine maleate [(I), code number 17]

A mixture of 4.5 g of E-5-[4-(3,4-methylenedioxy cinnamoyl) 1-piperizinyl]pentanoic acid [(If); code number 15], 0.9 ml of pyrrolidine, 1.8 g of 1-hydroxy benzotriazole, 1.5 ml of triethylamine and 2.3 g of D.C.C.I. in 100 ml of THF is left under agitation for 12 hours at 20° C. Then the insoluble portion is filtered, the filtrate evaporated and the residue is chromatographed on a silica column, (M.P.L.C.); by elution using the methylene chloride 98%-methanol 2% mixture, 3.8 g of the expected product was obtained in base form (Yield: 85%) which is dissolved in acetone. An acetone solution of maleic acid is added, then the mixture is cooled and the precipitate obtained is filtered which corresponds to the expected salt.

By the same process, but from the corresponding reagents, the compounds shown in table I under code numbers 2 to 4, 8 to 10, 18 to 20, 22, 23, 26 27, 29 to 31, 33, 35, 38, 40, 44, 45, 49 to 54, 56 to 59, 61, 65 and 66 are obtained as well as the compounds of formula (IIa).

EXAMPLE 4A

E-2-[4-(3,4-methylenedioxy cinnamoyl) 1-piperazinyl]2-pyrrolidino carbonyl ethyl, S(+) enantiomer [(I), code number 4]

To a solution of 2.5 g of E-2-piperazino 2-pyrrolidino carbonyl ethyl S(−) [(V)] in 50 ml of methylene chloride is added 1.2 g of triethylamine, then 2.5 g of the acid chloride of 3,4-methylenedioxy cinnamic acid (IV). It is left under agitation for 3 hours at 20° C., then washed with water, the organic phase is decanted and evaporated, the residue is taken up in 50 ml of 1N hydrochloric acid, filtered, the filtrate is washed with ethyl acetate, neutralized by means of $NH_4OH$, extracted with methylene chloride, dried on sodium or magnesium sulfate, filtered ans the filtrate is evaporated and the residue chromatographed on a silica column (M.P.L.C.). By elution using the methylene chloride 95%-methanol 5% mixture, 2.4 g of the expected product are obtained (Yield: 53%).

By the same process, but from the corresponding reagents, the compounds shown in table I under code numbers 2, 3, 6, 8 to 10, 17, 19, 20, 22, 23, 29 to 31, 33, 35, 38, 40, 49 to 54, 58, 59, 61, 65 and 66 are obtained, as well as the compounds of formula (IIa) and (IIIa).

EXAMPLE 4B

E-N-(3,4-dioxymethylene cinnamoyl) piperazine (II)

A mixture of 250 g of E-3,4-dioxymethylene cinnamic acid (IV) in 875 ml of thionyl chloride are heated to reflux for 40 minutes. Then the unreacted thionyl chloride is distilled, the residue is taken up in toluene, the toluene is evaporated, the residue is crystallized in petroleum ether and filtered (273 g). The product obtained is slowly added to 20° C. to a solution of 224 g of anhydrous piperazine in 1800 ml of acetic acid (solution previously obtained by slowly adding the piperazine to acetic acid at 40° C.). Then it is left under agitation for 12 hours, filtered, the filtrate is basified with NaOH pellets, the formed precipitate is extracted with methyl ethyl ketone, the obtained solution is evaporated and the residue crystallized in toluene. 110 g of the expected product are obtained.

Melting point: 135° C.
Yield: 32%
Empirical formula: $C_{14}H_6N_2O_3$
Molecular weight: 260.28
Elementary analysis:

|  | C | H | N |
|---|---|---|---|
| Calculated (%) | 64.60 | 6.20 | 10.76 |
| Obtained (%) | 64.29 | 6.27 | 10.50 |

EXAMPLE 5

E-4-(3,4-dioxymethylene cinnamoyl) 1-pyrrolidinocarbonylmethyl piperidine, hydrated hydrochloride [(I), code number 18]

A mixture of 5.4 g of piperonal (VI), 6.8 g of 4-acetyl 1-pyrrolidinocarbonylmethyl piperidine (VII) and 7.1 ml of concentrated NaOH in 80 ml of ethanol is left under agitation for 3 days at room temperature, then the solvents are evaporated, the residue is taken up in ethyl acetate, washed with water, dried on sodium or magnesium sulfate, filtered, the filtrate is evaporated and the residue chromatographed on a silica column (M.P.L.C.). By elution using the methylene chloride 96%—methanol 4% mixture, 5.5 g of an oily product were obtained which was dissolved in acetone, ≃6N hydrochloric ethanol is added, the mixture is cooled, the precipitate formed is filtered and recrystallized in absolute ethanol; thus 3.5 g (Yield: 30%) of the expected product were obtained.

By the same process, but from the corresponding reagents, the compounds shown in Table I under code number 26 and 27 were obtained.

EXAMPLE 6

E-N-4-[1-[4-(3,4-dioxymethylene cinnamoyl)piperazinyl]methylcarbonylamino]butyric acid [(I), code number 1]

To 50 ml of trifluoroacetic acid cooled to 5° C. is added, while stirring, a solution of 9.2 g of the tertiobutylic ester of E-4-[1-[4-(3,4-dioxymethylene cinnamoyl) piperazinyl]methylcarbonylamino]butyric acid (Id), prepared as described in the above examples 1, 2, 3 or 4A, in 20 ml of methylene chloride, without the temperature of the reaction medium exceeding 20° C. (addition in about 15 minutes). Then it is left under agitation for 12 hours, the solvents are evaporated, the residue is taken up in water, the aqueous phase is washed with ethyl ether, the pH is brought to ∼5 with NH$_4$OH, the mixture is extracted with ethyl acetate, the extract is dried on magnesium sulfate, filtered and the filtrate evaporated. The residue is crystallized in ethyl acetate, then recrystallized in methanol. 2.9 g of the expected product are thus obtained.

By the same process, but from the corresponding reagents, the compounds shown in Table I under the code numbers 11 to 16, 28, 32, 34, 36, 37, 39, 41 to 43, 48 and 67 are obtained.

EXAMPLE 7 tertiobutyl E-N-4-[2-[1-(4-methoxy3-hydroxy cinnamoyl)4-piperazino]acetamido]butanoate. (I)

A solution of 10.8 g of tertiobutyl E-N-4-[2-[1-(4-methoxy 3 isobutyloxycarbonyloxy cinnamoyl) 4-piperazino]acetamido]butanoate [(VIII), prepared according to example 2] in 150 ml of ammonia gaz saturated methanol for 2 days at 20° C. Then the solvents are evaporated and the residue is chromatographed on a silica column (H.P.L.C.). By eluting with the methylene chloride 95%—methanol 5% mixture and then with the methylene chloride 92.5%—methanol 7.5% mixture, 8.1 g of the expected product are obtained (Yield: 91%).

Empirical formula: C$_{24}$H$_{35}$N$_3$O$_6$
Molecular weight: 461.54

By the same process, but from the corresponding reagents, the compounds shown in Table I under code numbers 21 and 25 are obtained.

EXAMPLE 8

E-4-amino 1-(3,4-dioxymethylene cinnamoyl)piperidine (II)

A mixture of 10.2 g of E-4-trifluoromethylcarbonylamino 1-(3,4-dioxymethylene cinnamoyl)piperidine (IIa) and 24.5 g of K$_2$CO$_3$ in 250 ml of methanol and 100 ml of water is left under agitation for 12 hours at ambient temperature. Then the solvents are evaporated, the residue is taken up in chloroform, the mixture is washed with water, dried on sodium or magnesium sulfate, filtered and the filtrate is evaporated. Thus the expected crystallized product is obtained.

Melting point: 120° C.
Yield: ∼100%
Empirical formula: C$_{15}$H$_{18}$N$_2$O$_3$
Molecular weight: 274.31

By the same process, but from the corresponding reagents, the other compounds of formula (II) are obtained from the corresponding compounds (IIa), as well as the compounds of formula (V) from the compounds (XIV) and the compounds of formula (IIb) resulting from the condensation of the compounds (IVa) and (IX).

EXAMPLE 9

1-benzyl 4-trifluoromethylcarbonylamino piperidine (X)

To a solution cooled to 0° C. of 86 g of 1-benzyl 4-amino piperidine (XI) in 350 ml of pyridine are slowly added (in two hours) 75 ml of trifluoroacetic anhydride. Then it is left for 30 minutes between 0° and 10° C., the solution is poured into 1500 ml of iced water, extracted with ether, the extract is washed with water, dried on sodium or magnesium sulfate, filtered, the filtrate is evaporated, the residue is taken up in isopropylic ether, the insoluble portion is filtered and the filtrate is evaporated. Thus the expected crystallized product is obtained.

Melting point: 125° C. Yield: 72%
Empirical formula: C$_{14}$H$_{17}$F$_3$N$_2$O
Moleuclar weight: 286.29

By the same process, but from the corresponding reagents, the other compounds (X) are obtained.

EXAMPLE 10

4-trifluoromethylcarbonylamino piperidine (IX)

A suspension of 92 g of 1-benzyl 4-trifluoromethylcarbonylamino piperidine (X) and 9 g of wet 10% palladium on charcoal in 1000 ml of methanol is left under agitation for 8 days in a hydrogen atmosphere at room temperature. Then it is filtered, the filtrate is evaporated and the residue chromatographed on a silica column (M.P.L.C.). By eluting with pure methanol, 44 g of the expected product are obtained.

Melting point: 111° C.
Yield: 70%
Empirical formula: C$_7$H$_{11}$F$_3$N$_2$O
Molecular weight: 196.17

By the same process, but from the corresponding reagents, the other compounds (IX) are obtained.

EXAMPLE 11 iodomethylate of E-4-(3,4-methylenedioxycinnamoyloxy) 1-pyrrolidinocarbonylmethyl piperidine [(I), code number 62]

To a solution of 4.3 g of E-4-(3,4-methylenedioxycinnamoyloxy) 1-pyrrolidinocarbonylmethyl piperidine [(I), code number 61] in 50 ml of methylene chloride are added, at room temperature, 2.5 ml of methyl iodide, then it is left under agitation for 12 hours, sheltered from the air. Then it is filtered, the precipitate is washed on the filter with methylene chloride, then it is dried in a good vacuum. 5 g (Yield: 85%) of the expected product are obtained.

By the same process, but from the corresponding reagents, the compound shown under code number 55 in table I was obtained.

EXAMPLE 12

E-4-(3,4-methylenedioxycinnamoyl) 1-pyrrolidinocarbonylmethyl piperazine, N-oxide [(I), code number 60]

To a solution of 7.4 g of E-4-(3,4-methylenedioxycinnamoyl) 1-pyrrolidinocarbonylmethyl piperazine in 400 ml of chloroform are added, in small portions over 20 minutes at room temperature, 4.9 g of paranitroperbenzoic acid. Then it is left under agitation for 30 minutes and filtered, the filtrate is washed with a sodium bicarbonate solution, then with water, dried on sodium or magnesium sulfate, filtered and the filtrate evaporated. The residue is taken up in water and the aqueous phase is then continuously extracted using methylene chloride. The organic phase is then dried on sodium sulfate. Then it is fitlered, the filtrate is evaporated and the residue crystallized in ethyl ether. 5 g (Yield: 64.5%) of the expected product are obtained.

EXAMPLE 13

E-R-(−)-1-[1-[4-(3,4-dioxymethylene cinnamoyl) piperazinyl]1-pyrrolidinocarbonyl ethyl [(I), code number 5]

A suspension of 7 g of (+) binaphthyl phosphoric acid in 50 ml of methanol is heated to 50° C. Then a solution of 7.7 g of E-1-[1-[4-(3,4-dioxymethylene cinnamoyl)piperazinyl]] 1-pyrrolidinocarbonyl ethyl [(I), code number 3] in 20 ml of ethanol is introduced therein. It is left under agitation for 4 hours, then filtered, the precipitate is rinced with ethanol and dried at 80° C. in a good vacuum. 6.34 g of salt are obtained which is taken up in water, basified with $NH_2OH$, the solution obtained is extracted with ethyl acetate, the organic phase is evaporated and the residue chromatographed on a silica column. Eluted with the ethyl chloride 95%—methanol 5%, then methylene chloride 90%—methanol 10% mixtures, 1.76 g (Yield: 26%) of the expected product are obtained.

TABLE I $$E-Ar-C=C-CO-A-(CH_2)_m-C(R_2)(R_3)-(CH_2)_n-CO-B$$
$$\phantom{E-Ar-}R\phantom{=C-CO-A-(CH_2)_m-}R_1 \qquad (I)$$

| Code Number | Ar— | R | R₁ | COA— | m | R₂ | R₃ | n | —B | Form | Empirical formula | Molecular weight | Melting point (°C) | ELEMENTARY ANALYSIS OR [α]ᴅ |
|---|---|---|---|---|---|---|---|---|---|---|---|---|---|---|
| 1 | methylenedioxyphenyl | H | H | piperazine-CO | 0 | H | H | 0 | —NH(CH₂)₃—HOOC | Base | C₂₀H₂₅N₃O₆ | 403.42 | 165 | C.H.N. % C H N<br>Cal. 59.54 6.25 10.42<br>Obt. 59.18 6.35 10.24 |
| 2 | methylenedioxyphenyl | H | H | piperazine-CO | 1 | H | H | 0 | pyrrolidine | HCl | C₂₁H₂₈ClN₃O₄ | 421.91 | >260 | C.H.N.<br>Cal 59.78 6.69 9.96<br>Obt. 59.75 6.94 9.83 |
| 3 | methylenedioxyphenyl | H | H | piperazine-CO | 0 | CH₃ | H | 0 | pyrrolidine (±) | HCl + 1.15% H₂O | C₂₁H₂₈ClN₃O₄ + 1.15% H₂O | 426.82 | 252 | C.H.N. (+1.15% H₂O)<br>Cal. 59.09 6.74 9.85<br>Obt. 59.11 6.68 9.75 |
| 4 | methylenedioxyphenyl | H | H | piperazine-CO | 0 | CH₃ | H | 0 | pyrrolidine (S+) | Base + 2.5% H₂O | C₂₁H₂₇N₃O₄ + 2.5% H₂O | 395.33 | vitrous product | C.H.N. (+2.5% H₂O)<br>Cal. 63.79 7.25 10.63<br>Obt. 63.52 7.55 10.50<br>$[α]_D^{20} = +29.8°$<br>(C = 1% CHCl₃) |
| 5 | methylenedioxyphenyl | H | H | piperazine-CO | 0 | CH₃ | H | 0 | pyrrolidine (R−) | Base + 3.13% H₂O | C₂₁H₂₇N₃O₄ + 3.13% H₂O | 397.90 | vitrous product | C.H.N. (+3.13% H₂O)<br>Cal. 63.38 7.19 10.56<br>Obt. 63.41 7.31 10.17<br>$[α]_D^{20} = -29.7°$<br>(C = 1% CHCl₃) |
| 6 | methylenedioxyphenyl | H | H | piperazine-CO | 0 | H | H | 0 | 2-oxo-pyrrolidine | Base | C₂₀H₂₃N₃O₅ | 385.41 | 163 | C.H.N. (+4.2% H₂O)<br>Cal. 62.32 6.02 10.90<br>Obt. 62.03 6.02 10.82 |

TABLE I-continued $$E-Ar-C\equiv C-CO-A-(CH_2)_m-\overset{R_2}{\underset{R_3}{C}}-(CH_2)_n-CO-B \quad (I)$$
$$\phantom{E-Ar-C\equiv C-}\overset{|}{\underset{R}{}}\phantom{-CO-A-(CH_2)_m-}\overset{|}{\underset{R_1}{}}$$

| Code Number | Ar— | R | R₁ | COA— | m | R₂ | R₃ | n | —B | Form | Empirical formula | Molecular weight | Melting point (°C.) | | ELEMENTARY ANALYSIS OR [α]p | | | |
|---|---|---|---|---|---|---|---|---|---|---|---|---|---|---|---|---|---|---|
| | | | | | | | | | | | | | | | % | C | H | N |
| 7 |  | H | H |  | 0 | H | H | 0 | 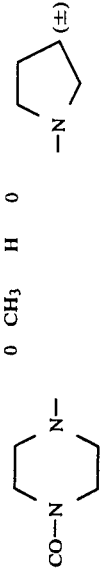 | HCl + 4.2% H₂O | C₂₃H₃₄ClN₃O₅ + 4.2% H₂O | 488.55 | 200 | Cal. Obt. | | 56.54 56.58 | 7.41 7.20 | 8.60 8.57 |
| 8 |  | H | H | 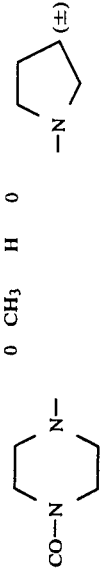 | 0 | CH₃ | H | 0 |  (±) | Base | C₂₀H₂₆ClN₃O₂ | 375.89 | 170 | C.H.N. Cal. Obt. | | 63.90 63.85 | 6.97 7.09 | 11.18 10.91 |
| 9 |  | H | H |  | 0 | CH₃ | H | 0 |  (±) | Base | C₂₀H₂₆ClN₃O₂ | 375.89 | 100 | C.H.N. Cal. Obt. | | 63.90 63.90 | 6.97 7.32 | 11.18 10.87 |
| 10 | 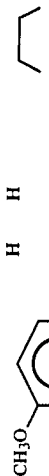 | H | H |  | 0 | CH₃ | H | 0 |  (±) | Base | C₂₀H₂₆FN₃O₂ | 359.43 | 143 | C.H.N. Cal. Obt. | | 66.83 66.90 | 7.29 7.60 | 11.69 11.46 |
| 11 |  | H | H |  | 0 | H | H | 0 | —NH—(CH₂)₃ HOOC | HCl + 4.5% H₂O | C₂₀H₂₈ClN₃O₆ + 4.5% H₂O | 462.53 | 110 | C.H.N. (+4.5% H₂O) Cal. Obt. | | 51.94 51.91 | 6.61 6.74 | 9.09 8.94 |
| 12 |  | H | H |  | 0 | H | H | 0 | —NH—(CH₂)₃ HOOC | HCl + 1.9% H₂O | C₂₀H₂₈ClN₃O₆ + 1.9% H₂O | 450.51 | 200 110 | C.H.N. (+1.9% H₂O) Cal. Obt. | | 53.32 53.45 | 6.48 6.23 | 9.33 9.61 |
| | | | | | | | | | | | | | | C.H.N. (+4% H₂O) | | | | |

TABLE I-continued $$E-Ar-C=C-CO-A-(CH_2)_m-\overset{R_2}{\underset{R_3}{\overset{|}{\underset{|}{C}}}}-(CH_2)_n-CO-B \quad (I)$$
$$\phantom{E-Ar-C=C-CO-}\overset{|}{R}\phantom{-A-(CH_2)_m-}\overset{|}{R_1}$$

| Code Number | Ar— | R | R₁ | COA— | m | R₂ | R₃ | n | —B | Form | Empirical formula | Molecular weight | Melting point (°C.) | | ELEMENTARY ANALYSIS OR [α]$_D$ | | | |
|---|---|---|---|---|---|---|---|---|---|---|---|---|---|---|---|---|---|---|
| | | | | | | | | | | | | | | % | | C | H | N |
| 13 |  | H | H |  | 0 | H | H | 0 | —NH—(CH₂)₃COOH | HCl + 4% H₂O | C₁₉H₂₆ClN₃O₆ + 4% H₂O | 445.71 | >210 | C.H.N. Cal. Obt. | | 51.20 51.49 | 6.33 6.15 | 9.43 9.30 |
| 14 | 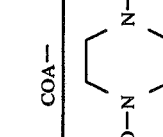 | H | H | 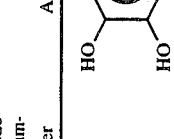 | 1 | H | H | 1 | —OH | HCl + 5.23% H₂O | C₁₈H₂₃ClN₂O₅ + 5.23% H₂O | 403.96 | 140 | C.H.N. Cal. Obt. | (+5.23% H₂O) | 53.52 53.63 | 6.33 6.08 | 6.94 7.00 |
| 15 | 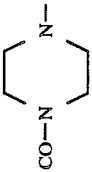 | H | H |  | 1 | H | H | 2 | —OH | HCl + 4.8% H₂O | C₁₉H₂₅ClN₂O₅ + 4.8% H₂O | 416.70 | 214 | C.H.N. Cal. Obt. | (+4.8% H₂O) | 54.76 55.00 | 6.58 6.74 | 6.72 6.77 |
| 16 |  | H | H | 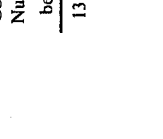 | 1 | H | H | 0 | —OH | HCl + 0.6% H₂O | C₁₇H₂₁ClN₂O₅ + 0.6% H₂O | 370.89 | >260 | C.H.N. Cal. Obt. | (+0.6% H₂O) | 55.05 55.01 | 5.77 5.57 | 7.55 7.76 |
| 17 | 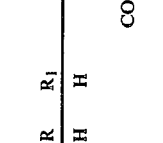 | H | H | 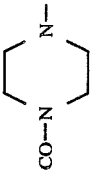 | 1 | H | H | 2 |  | Maleate | C₂₇H₃₅N₃O₈ | 529.57 | 179 | C.H.N. Cal. Obt. | | 61.23 61.35 | 6.66 6.88 | 7.94 7.84 |
| 18 |  | H | H |  | 0 | H | H | 0 |  | HCl + 2% H₂O | C₂₁H₂₇ClN₂O₄ + 2% H₂O | 415.20 | 205 | C.H.N. Cal. Obt. | (+2% H₂O) | 60.74 60.50 | 6.78 7.16 | 6.75 6.60 |
| 19 | 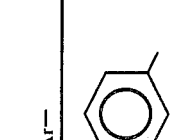 | H | H |  | 0 | CH₃ | H | 0 | 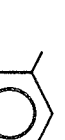 (±) | HCl | C₂₁H₃₀ClN₃O₃ | 407.93 | >200 | C.H.N. Cal. Obt. C.H.N. | | 61.83 61.71 | 7.41 7.64 | 10.30 10.35 |

TABLE I-continued $$E-Ar-C=C-CO-A-(CH_2)_m-C(R_2)(R_3)-(CH_2)_n-CO-B \quad (I)$$
$$\phantom{E-Ar-C}|\phantom{-CO-A-(CH_2)_m-}$$
$$\phantom{E-Ar-}R\ R_1$$

| Code Number | Ar— | R | R₁ | COA— | m | R₂ | R₃ | n | —B | Form | Empirical formula | Molecular weight | Melting point (°C.) | | ELEMENTARY ANALYSIS OR $[\alpha]_D$ | | | |
|---|---|---|---|---|---|---|---|---|---|---|---|---|---|---|---|---|---|---|
| | | | | | | | | | | | | | | | % | C | H | N |
| 20 | methylenedioxyphenyl | H | H | piperazine-CO-N | 1 | H | H | 1 | pyrrolidine | Maleate | $C_{26}H_{33}N_3O_8$ | 515.55 | 158 | C.H.N. | Cal. Obt. | 60.57 60.57 | 6.45 6.65 | 8.15 8.07 |
| 21 | 4-hydroxyphenyl | H | H | piperazine-CO-N | 0 | $CH_3$ | H | 0 | pyrrolidine | HCl | $C_{20}H_{28}ClN_3O_3$ | 395.90 | 120 (decomposition) | C.H.N. | Cal. Obt. | 60.98 60.72 | 7.17 7.50 | 10.67 10.35 |
| 22 | 3,4,5-trimethoxyphenyl | H | H | piperidine-CONH | 0 | H | H | 0 | pyrrolidine | HCl | $C_{23}H_{34}ClN_3O_5$ | 467.98 | ≃260 | C.H.N. | Cal. Obt. | 59.03 58.70 | 7.32 7.68 | 8.98 8.67 |
| 23 | methylenedioxyphenyl | H | H | piperidine-CONH | 0 | H | H | 0 | pyrrolidine | HCl + 1.25% H₂O | $C_{21}H_{28}ClN_3O_4$ + 1.25% H₂O | 427.26 | ≃260 | C.H.N. (+1.25% H₂O) | Cal. Obt. | 59.03 58.61 | 6.75 6.91 | 9.84 9.60 |
| 24 | methylenedioxyphenyl | H | H | piperidine-NH | 0 | H | H | 0 | pyrrolidine | HCl | $C_{21}H_{28}ClN_3O_4$ | 421.91 | >260 | C.H.N. | Cal. Obt. | 59.78 59.53 | 6.69 6.72 | 9.96 9.75 |
| 25 | 4-hydroxyphenyl | H | H | piperazine-CO-N | 0 | $CH_3$ | H | 0 | pyrrolidine | HCl | $C_{20}H_{28}ClN_3O_3$ | 393.90 | 100 (decomposition) | C.H.N. (+3.5% H₂O) | Cal. Obt. | 60.98 60.92 | 7.17 7.30 | 10.67 10.40 |

TABLE I-continued $$E-Ar-\underset{\underset{R_1}{|}}{\overset{\overset{R_2}{|}}{C}}=C-CO-A-(CH_2)_m-\underset{\underset{R_3}{|}}{C}-(CH_2)_n-CO-B \quad (I)$$

| Code Number | Ar | R | R₁ | COA— | m | R₂ | R₃ | n | —B | Form | Empirical formula | Molecular weight | Melting point (°C.) | | ELEMENTARY ANALYSIS OR [α]$_D$ | | | |
|---|---|---|---|---|---|---|---|---|---|---|---|---|---|---|---|---|---|---|
| | | | | | | | | | | | | | | | % | C | H | N |
| 26 | 3,4,5-(CH₃O)₃-C₆H₂ | H | H |  | 0 | H | H | 0 |  | HCl + 3.5% H₂O | C₂₃H₃₃ClN₂O₅ + 3.5% H₂O | 469.40 | 148 | C.H.N. Cal. Obt. | | 58.05 7.47 5.97<br>58.82 7.39 6.12 | | |
| 27 | 3,4,5-(CH₃O)₃-C₆H₂ | H | H |  | 0 | H | H | 0 |  | Oxalate + 1% H₂O | C₂₄H₃₄N₂O₉ + 1% H₂O | 499.52 | 105 | C.H.N. (+1% H₂O) Cal. Obt. | | 57.71 6.97 5.61<br>57.31 6.82 5.60 | | |
| 28 | 3,4-methylenedioxy-C₆H₃ | H | H |  | 0 | CH₃ | H | 0 | —NH—CH₂COOH | hemifumarate + 0.54% H₂O | C₁₂H₂₅N₃O₈ + 0.54% H₂O | 449.86 | 110 | C.H.N. (+0.54% H₂O) Cal. Obt. | | 56.07 5.66 9.34<br>55.84 5.86 9.18 | | |
| 29 | 3,4-methylenedioxy-C₆H₃ | H | H |  | 0 | CH₃ | H | 0 | —NHCH₂CONH₂ | HCl + 2.1% H₂O | C₁₉H₂₅ClN₄O₅ + 2.1% H₂O | 433.99 | 150 | C.H.N. (+2.1% H₂O) Cal. Obt. | | 52.58 6.03 12.91<br>52.85 6.13 12.87 | | |
| 30 | 3,4-methylenedioxy-C₆H₃ | H | CH₃ |  | 0 | H | H | 0 |  | Base HCl | C₂₁H₂₇N₃O₄<br>C₂₁H₂₈ClN₃O₄ | 385.40<br>421.91 | 102<br>200 | C.H.N. (HCl) Cal. Obt. | | 59.78 6.69 9.96<br>59.64 6.98 9.60 | | |
| 31 | 3,4-methylenedioxy-C₆H₃ | CH₃ | H |  | 0 | H | H | 0 |  | HCl + 4.22% H₂O | C₂₁H₂₈ClN₃O₄ + 4.22% H₂O | 440.50 | 176 | C.H.N. (+4.22% H₂O) Cal. Obt. | | 57.26 6.88 9.54<br>57.38 6.81 9.33 | | |
| | | | | | | | | | | | | | | C.H.N. (+2.7% H₂O) | | | | |

TABLE I-continued $$E-Ar-C=C-CO-A-(CH_2)_m-C(R_2)(R_3)-(CH_2)_n-CO-B \quad (I)$$
$$\phantom{E-Ar-}R\phantom{=}R_1$$

| Code Number | Ar— | R | R₁ | COA— | m | R₂ | R₃ | n | —B | Form | Empirical formula | Molecular weight | Melting point (°C.) | ELEMENTARY ANALYSIS OR [α]$_D$ | | | |
|---|---|---|---|---|---|---|---|---|---|---|---|---|---|---|---|---|---|
| | | | | | | | | | | | | | | % | C | H | N |
| 32 | 4-Cl-C₆H₄— | H | H | piperazine-CON | 0 | CH₃ | H | 0 | —OH (±) | Base + 2.7% H₂O | C₁₆H₁₉ClN₂O₃ + 2.7% H₂O | 331.74 | 120 (decomposition) | C.H.N. Cal. Obt. | 57.92 57.63 | 6.07 6.17 | 8.44 7.96 |
| 33 | 3,4-methylenedioxyphenyl | —H | —H | piperazine-CON | 0 | Et | H | 0 | pyrrolidinyl (±) | Base | C₂₂H₂₉N₃O₄ | 399.48 | 95 | C.H.N Cal Obt. | 66.14 66.11 | 7.32 7.33 | 10.52 10.44 |
| 34 | 3,4-methylenedioxyphenyl | —H | —H | piperazine-CON | 1 | H | H | 0 | —OH | HCl + 5.5% H₂O | C₂₀H₂₇ClN₂O₅ + 5.5% H₂O | 434.80 | 120 | C.H.N. Cal. Obt. | (+5.5% H₂O) 55.24 55.31 | 6.87 6.91 | 6.44 6.65 |
| 35 | 3,4-methylenedioxyphenyl | —H | —H | piperazine-CON | 1 | H | H | 3 | pyrrolidinyl | HCl | C₂₄H₃₄N₃O₄ | 463.99 | 194 | C.H.N Cal Obt. | 62.12 62.39 | 7.39 7.28 | 9.06 8.98 |
| 36 | 3,4-methylenedioxyphenyl | —H | —H | piperazine-CON | 0 | H | H | 0 | —NHCH₂COOH | Base | C₁₈H₂₁N₃O₆ | 375.37 | 220 | C.H.N. Cal. Obt. | 57.59 57.40 | 5.64 5.81 | 11.20 10.92 |
| 37 | 4-F-C₆H₄— | —H | —H | piperazine-CO-N | 0 | CH₃ | H | 0 | —OH (±) | HCl | C₁₆H₂₀FN₃O₃ | 342.79 | 100 (decomposition) | C.H.N Cal. Obt. | 56.06 55.87 | 5.88 5.68 | 8.17 8.19 |
| 38 | 3,4-methylenedioxyphenyl | —H | —H | piperazine-CO-N | 0 | H | H | 0 | —NH—(CH₂)₂—N(CH₃)₂ | di HCl + 0.9% H₂O | C₂₀H₃₀Cl₂N₄O₄ + 0.9% H₂O | 465.43 | 222 (decomposition) | C.H.N. Cal. Obt. C.H.N. | (+0.9% H₂O) 51.61 51.56 (+2.5% H₂O) | 6.59 6.53 | 12.03 11.90 |

TABLE I-continued $$E-Ar-\underset{R}{\underset{|}{C}}=\underset{R_1}{\underset{|}{C}}-CO-A-(CH_2)_m-\underset{R_3}{\underset{|}{\overset{R_2}{C}}}-(CH_2)_n-CO-B \quad (I)$$

| Code Number | Ar— | R | R₁ | COA— | m | R₂ | R₃ | n | —B | Form | Empirical formula | Molecular weight | Melting point (°C.) | ELEMENTARY ANALYSIS OR [α]$_D$ | | | | |
|---|---|---|---|---|---|---|---|---|---|---|---|---|---|---|---|---|---|---|
| | | | | | | | | | | | | | | | % | C | H | N |
| 39 | 3,4-methylenedioxyphenyl (Ar with OCH₂O) | —H | —H | piperazine-CO— | 0 | H | H | 0 | —NH(CH₂)₂HOOC | HCl + 2.5% H₂O | C₁₉H₂₄ClN₃O₆ + 2.5% H₂O | 436.78 | 120 | C.H.N. Cal. Obt. | | 52.24 52.33 | 5.82 6.02 | 9.62 9.62 |
| 40 | 3,4-methylenedioxyphenyl | —H | —H | piperazine-CO— | 0 | H | H | 0 | —NH—(CH₃)₂CONH₂ | HCl | C₁₉H₂₅ClN₄O₅ | 424.88 | 180 | C.H.N. Cal. Obt. | | 53.71 53.46 | 5.93 6.09 | 13.19 12.88 |
| 41 | 4-Cl-phenyl | H | H | piperazine-CO— | 0 | CH₃ | H | 0 | —OH (±) | HBr | C₁₆H₂₀BrClN₂O₃ | 403.70 | 220 (decomposition) | C.H.N. Cal. Obt. | | 47.60 47.70 | 4.99 5.02 | 6.94 7.05 |
| 42 | 4-HO-phenyl | H | H | piperazine-CO— | 0 | CH₃ | H | 0 | —OH (±) | Base + 5.4% H₂O | C₁₆H₂₀N₂O₄ + 5.4% H₂O | 321.71 | 225 (decomposition) | C.H.N. (+5.4% H₂O) Cal. Obt. | | 59.73 59.52 | 6.86 6.70 | 8.71 8.61 |
| 43 | 4-HO-phenyl | H | H | piperazine-CO— | 0 | H | H | 0 | —OH (±) | Base + 2.6% H₂O | C₁₆H₂₀N₂O₄ + 2.6% H₂O | 312.33 | >250 | C.H.N. (+2.6% H₂O) Cal. Obt. | | 61.51 61.61 | 6.74 6.79 | 8.97 8.89 |
| 44 | 3,4,5-trimethoxyphenyl | H | H | 4-(N-CH₃)piperidine-CON | 0 | H | H | 0 | pyrrolidine-N | 1.3 oxalate + 1.5% H₂O | C₂₄H₃₅N₃O₅ + 1.3 oxalate + 1.5% H₂O | 571.16 | 105 | C.H.N. (1.3 oxalate + 1.5% H₂O) Cal. Obt. | | 55.93 55.66 | 6.87 7.07 | 7.36 7.34 |
| | | | | | | | | | | | | | | C.H.N. (+1% H₂O) | | | | |

TABLE I-continued $$E-Ar-C=C-CO-A-(CH_2)_m-\underset{R_3}{\overset{R_2}{\underset{|}{C}}}-(CH_2)_n-CO-B \quad (I)$$
$$\phantom{E-Ar-}\underset{R}{|}\phantom{=C-CO-A-(CH_2)_m-}\underset{R_1}{|}$$

| Code Number | Ar— | R | R₁ | COA— | m | R₂ | R₃ | n | —B | Form | Empirical formula | Molecular weight | Melting point (°C.) | | ELEMENTARY ANALYSIS OR [α]$_D$ | C | H | N |
|---|---|---|---|---|---|---|---|---|---|---|---|---|---|---|---|---|---|---|
| 45 | methylenedioxyphenyl | H | H | 4-(N-CH₃)piperidinyl-CO-N | 0 | H | H | 0 | pyrrolidinyl | Oxalate + 1% H₂O | C₂₄H₃₁N₃O₈ + 1% H₂O | 494.46 | 142 | C.H.N. Cal. Obt. | % | 58.29 57.90 | 6.43 6.30 | 8.49 8.07 |
| 46 | 3,4,5-trimethoxyphenyl | H | H | 4-NH-piperidinyl-CO-N | 0 | CH₃ | H | 0 | pyrrolidinyl (±) | HCl + 1.6% H₂O | C₂₄H₃₆ClN₃O₅ + 1.6% H₂O | 489.94 | 244 | C.H.N. (+1.6% H₂O) Cal. Obt. | | 55.83 58.55 | 7.59 7.65 | 8.58 9.44 |
| 47 | methylenedioxyphenyl | H | H | 4-NH-piperidinyl-CO-N | 0 | CH₃ | H | 0 | pyrrolidinyl (±) | HCl + 1.9% H₂O | C₂₂H₃₀ClN₃O₄ + 1.9% H₂O | 444.38 | 240 | C.H.N. (+1.9% H₂O) Cal. Obt. | | 59.45 59.49 | 7.02 7.10 | 9.46 9.26 |
| 48 | methylenedioxyphenyl | H | H | piperazinyl-CON | 0 | CH₃ | H | 0 | —NH—(CH₂)₂ HOOC (±) | Base + 4.8% H₂O | C₂₀H₂₅N₃O₆ + 4.8% H₂O | 423.59 | 100 | C.H.N. (+4.8% H₂O) Cal. Obt. | | 56.71 56.72 | 6.48 6.59 | 9.92 10.08 |
| 49 | methylenedioxyphenyl | H | H | piperazinyl-CON | 0 | CH₃ | H | 0 | —NH—(CH₂)₂ HOOC | Base | C₂₀H₂₆N₄O₅ | 402.44 | 183 | C.H.N. Cal Obt. | | 59.69 59.57 | 6.51 6.69 | 13.92 13.89 |
| 50 | methylenedioxyphenyl | H | H | piperazinyl-CON | 0 | H | H | 0 | —NH—(CH₂)₂—N(Et)₂ | di HCl + 1.05% H₂O | C₂₂H₃₄Cl₂N₄O₄ + 1.05% H₂O | 494.63 | 220 | C.H.N. (+1.05% H₂O) Cal. Obt. C.H.N. | | 53.41 53.42 | 7.05 7.10 | 11.33 11.05 |

TABLE I-continued $$E-Ar-\underset{R}{\overset{R_1}{C}}=\underset{}{\overset{}{C}}-CO-A-(CH_2)_m-\underset{R}{\overset{R_2}{\underset{|}{C}}}-(CH_2)_n-CO-B \quad (I)$$

| Code Number | Ar— | R | R₁ | COA— | m | R₂ | R₃ | n | —B | Form | Empirical formula | Molecular weight | Melting point (°C.) | | ELEMENTARY ANALYSIS OR [α]_D | | | |
|---|---|---|---|---|---|---|---|---|---|---|---|---|---|---|---|---|---|---|
| | | | | | | | | | | | | | | | % | C | H | N |
| 51 | [methylenedioxy-methylphenyl] | H | H | [piperazine-CON] | 0 | C₃H₇ n | H | 0 | [pyrrolidine-N] (±) | Maleate | C₂₇H₃₅N₃O₈ | 529.57 | 200 | C.H.N. Cal Obt. | 61.23 61.09 | 6.66 6.76 | 7.94 7.98 |
| 52 | [methylenedioxy-methylphenyl] | H | H | [piperazine-CON] | 0 | CH₃ | CH₃ | 0 | [pyrrolidine-N] | Base + 0.9% H₂O | C₂₂H₂₉N₃O₄ + 0.9% H₂O | 403.02 | 165 | C.H.N. (+0.9% H₂O) Cal. Obt. | 65.56 65.70 | 7.36 7.56 | 10.43 10.21 |
| 53 | [methylenedioxy-methylphenyl] | H | H | [piperazine-CON] | 0 | C₃H₇ iso | H | 0 | [pyrrolidine-N] (±) | Base | C₂₂H₃₁N₃O₄ | 413.50 | 100 | C.H.N. Cal Obt. | 66.80 66.52 | 7.56 7.69 | 10.16 9.87 |
| 54 | [methylenedioxy-methylphenyl] | H | H | [piperazine-CON] | 0 | H | H | 0 | [CH₃-N-CH₃ / CH₂CH₂O—] | 1.5 Maleate | C₂₆H₃₃N₃O₁₁ | 563.55 | 154 | C.H.N. Cal Obt. | 55.41 55.13 | 5.90 5.93 | 7.46 7.36 |
| 55 | [methylenedioxy-methylphenyl] | H | H | [piperazine-CON] | 0 | H | H | 0 | [CH₃-N⁺(CH₃)CH₃ I⁻ / CH₂CH₂O—] | — | C₂₁H₃₀IN₃O₅ | 531.38 | 222 | C.H.N. Cal Obt. | 47.46 47.32 | 5.59 5.82 | 7.91 7.91 |
| 56 | [methylenedioxy-methylphenyl] | H | H | [bicyclic piperazine-CON] | 0 | H | H | 0 | [piperidine-N] | Base + 4% H₂O | C₂₂H₂₇N₃O₄ + 4% H₂O | 413.36 | 220 (decomposition) | C.H.N. (+4% H₂O) Cal. Obt. | 63.82 63.63 | 7.03 7.18 | 10.15 10.26 |
| 57 | [methylenedioxy-methylphenyl] | H | H | [2-methylpiperazine-CON] | 0 | H | H | 0 | [piperidine-N] | HCl | C₂₁H₂₈ClN₃O₄ | 421.91 | | C.H.N. (+0.75% H₂O) Cal Obt. | 59.78 59.60 | 6.69 6.84 | 9.96 10.15 |

TABLE I-continued $$E-Ar-\underset{R}{\underset{|}{C}}=\underset{R_1}{\underset{|}{C}}-CO-A-(CH_2)_m-\underset{R_3}{\underset{|}{\overset{R_2}{C}}}-(CH_2)_n-CO-B \quad (I)$$

| Code Number | Ar— | R | R₁ | COA— | m | R₂ | R₃ | n | —B | Form | Empirical formula | Molecular weight | Melting point (°C.) | | ELEMENTARY ANALYSIS OR [α]ᴅ | | | |
|---|---|---|---|---|---|---|---|---|---|---|---|---|---|---|---|---|---|---|
| | | | | | | | | | | | | | | % | C | H | N |
| 58 | 4-methyl-2,2-dimethyl-benzodioxole | H | H | piperazine-CON | 0 | H | H | 0 | pyrrolidine-N | 1.5 oxalate + 0.75% H₂O | C₂₅H₃₂N₃O₁₀ + 0.75% H₂O | 538.57 | 220 | Cal. Obt. | 55.74 55.90 | 6.06 6.11 | 7.80 7.82 |
| 59 | 4-methyl-methoxyphenyl | H | H | piperazine-CON | 0 | CH₃ | H | 0 | —OH | HBr | C₁₇H₂₃BrN₂O₄ | 399.28 | 220 (decomposition) | C.H.N. Cal. Obt. | 51.13 50.96 | 5.81 5.96 | 7.02 7.07 |
| 60 | methylenedioxy-methylphenyl | H | H | piperazine-N-oxide-CON | 0 | H | H | 0 | pyrrolidine-N | +3% H₂O | C₂₀H₂₅N₃O₅ + 3% H₂O | 399.41 | 150 (decomposition) | C.H.N. Cal Obt. | 60.14 59.99 | 6.63 6.68 | 10.52 10.60 |
| 61 | methylenedioxy-methylphenyl | H | H | piperidine-CO-O | 0 | H | H | 0 | pyrrolidine-N | HCl + 6.5% H₂O | C₂₁H₂₇ClN₂O₅ + 6.5% H₂O | 452.30 | 175 then 250 | C.H.N. Cal. Obt. | (+6.5% H₂O) 55.76 55.91 | 6.75 6.69 | 6.19 6.09 |
| 62 | methylenedioxy-methylphenyl | H | H | N-methylpiperidinium-COO | 0 | H | H | 0 | pyrrolidine-N | — | C₂₂H₂₉N₂O₅I | 528.37 | 212 | C.H.N. Cal. Obt. | 50.01 49.84 | 5.53 5.51 | 5.30 5.37 |
| 63 | methylenedioxy-methylphenyl | H | H | bicyclic NH—CON H(β) | 0 | H | H | 0 | pyrrolidine-N | HCl + 1% H₂O | C₂₃H₂₉N₃O₄ + 1% H₂O | 452.48 | >260 | C.H.N. Cal. Obt. C.H.N. | (+1% H₂O) 61.05 60.24 | 6.79 6.80 | 9.29 9.11 |

TABLE I-continued $$E-Ar-C=C-CO-A-(CH_2)_m-C(R_2)(R_3)-(CH_2)_n-CO-B \quad (I)$$
$$\phantom{E-Ar-C=}R\phantom{C-}R_1$$

| Code Number | Ar— | R | R₁ | COA— | m | R₂ | R₃ | n | —B | Form | Empirical formula | Molecular weight | Melting point (°C.) | ELEMENTARY ANALYSIS OR $[\alpha]_D$ | | | |
|---|---|---|---|---|---|---|---|---|---|---|---|---|---|---|---|---|---|
| | | | | | | | | | | | | | | | % | C | H | N |
| 64 | 3,4,5-(CH₃O)₃-C₆H₂ | H | H | 3-CH₃-piperazinyl-CO | 0 | H | H | 0 | pyrrolidinyl | Base | C₂₃H₃₃N₃O₅ | 431.52 | 100 (decomposition) | Cal. Obt. | 64.01 63.69 | 7.71 7.80 | 9.74 9.69 |
| 65 | 3,4,5-(CH₃O)₃-C₆H₂ | H | H | 3-CH₃-piperazinyl-CO | 0 | H | H | 0 | pyrrolidinyl | Base + 1.8% H₂O | C₂₃H₃₃N₃O₅ + 1.8% H₂O | 439.43 | 50 (decomposition) | C.H.N. Cal. Obt. | (+1.8% H₂O) 62.86 63.00 | 7.77 7.87 | 9.56 9.61 |
| 66 | 3,4-methylenedioxy-6-CH₃-C₆H₂ | H | H | 3-CH₃-piperazinyl-CO | 0 | H | H | 0 | pyrrolidinyl | HCl + 3% H₂O | C₂₁H₂₈ClN₃O₄ + 3% H₂O | 434.96 | 50 (decomposition) | C.H.N. Cal. Obt. | (+3% H₂O) 58.17 57.65 | 6.83 7.38 | 9.66 9.93 |
| 67 | 3,4,5-(CH₃O)₃-C₆H₂ | H | H | piperazinyl-CO | 0 | CH₃ | H | 0 | —OH (±) | Base + 3.75% H₂O | C₁₉H₂₆N₂O₆ + 3.75% H₂O | 393.43 | 202 | C.H.N. Cal. Obt. | (+3.75% H₂O) 58.04 58.12 | 7.09 6.58 | 7.12 7.03 |
| 68 | 3,4,5-(CH₃O)₃-C₆H₂ | H | H | piperazinyl-CO | 0 | CH₃ | H | 0 | pyrrolidinyl | Base + 1.63% H₂O | C₂₄H₃₅N₃O₅ + 1.63% H₂O | 452.93 | 50 (decomposition) | C.H.N. Cal. Obt. | (+1.63% H₂O) 63.63 63.83 | 7.97 8.11 | 9.28 9.35 |
| | | | | | | | | | | | | | | C.H.N. | (+2.6% H₂O) | | |

TABLE I-continued $$E-Ar-C=C-CO-A-(CH_2)_m \underset{R_3}{\overset{R_2}{\mid}} (CH_2)_n-CO-B \quad (I)$$
$$\phantom{E-Ar-C=C}R\phantom{-C}R_1$$

| Code Number | Ar— | R | R₁ | COA— | m | R₂ | R₃ | n | —B | Form | Empirical formula | Molecular weight | Melting point (°C.) | | ELEMENTARY ANALYSIS OR [α]ᴅ | | |
|---|---|---|---|---|---|---|---|---|---|---|---|---|---|---|---|---|---|
| | | | | | | | | | | | | | | % | C | H | N |
| 69 | (3-ethoxy-4-methylphenyl) | H | H | CO-N(CH₃)-piperazine-CO— | 0 | H | H | 0 | pyrrolidinyl | Base + 2.6% H₂O | C₂₂H₂₉N₃O₄ + 2.6% H₂O | 410.10 | 50 (decomposition) | Cal. Obt. | 64.43 64.38 | 7.42 7.51 | 10.25 10.15 |

The compounds of the invention were tested on laboratory animals and showed pharmacological activities and particularly stimulating, protecting and/or correcting activities of the cerebral functions.

These activities were demonstrated more especially by the test for mnesic retention of exploratory activity in accordance with the following method.

In an ACTIMETRE APELAB [BOISSIER and SIMON, Arch. Inter. Pharmacodyn. 158, 212, (1965)] apparatus the exploratory activity of male SWISS-WEBSTER mice was measured, then the animals received an intraperitoneal (or oral) injection of the compounds of the invention or of physiological serum. After a week, the exploratory activity c of the treated animals was again measured and the effect on mnesic retention was measured by habituation, i.e. a statistically significant reduction (t of STUDENT by paired groups) of the exploratory activity. To illustrate the invention, we give in table II below the results obtained with some compounds of the invention. The approximate acute toxicity was measured by the method described by MILLER and TAINTER in Proc. Soc. Exp. Biol. Med. 57, 261 (1944). The results obtained with some compounds of the invention are also shown by way of examples in this table II.

TABLE II

| Code Numbers of the Compounds Tested | Mnesic retention test | | Acute toxicity (mice) | |
|---|---|---|---|---|
| | Dose (mice) mg/kg/i.p. | % reduction of the exploratory activity | Dose mg/kg/i.p. | Mortality % |
| 1 | 10 | 26.3 | — | — |
| 2 | 1 | 21.8 | 400 | 0% |
| 6 | 0.01 | 22.7 | 400 | 0% |
| 9 | 0.1 | 30.5 | " | " |
| 17 | 0.01 | 23.9 | " | " |
| 18 | 0.01 | 21.6 | " | " |
| 22 | 0.01 | 21.3 | " | " |
| 23 | 0.01 | 33.5 | " | " |
| 31 | 0.01 | 26.5 | " | " |
| 34 | 0.001 | 24.9 | " | " |
| 47 | 0.1 | 26.9 | " | " |

As these results show, the compounds of the invention have a marked pharmacological activity and a low toxicity. The pharmaceutically acceptable compounds of the invention find then their application in therapeutics as useful drugs more particularly for stimulating intellectual efficiency in normal subjects, for preserving the cerebral function in aged subjects and for treating troubles of alertness and or memorization, following different pathologies, particularly cranial traumatisms, cerebral stocks and acute or sub-acute cerebrovascular accidents.

The present invention further extends to the pharmaceutical compositions containing, as active ingredient, one at least of the above-defined drugs these compositions being formulated particularly with a view to oral or parenteral administration. Thus, they may for example be administered orally in the form of pills, capsules, tablets or of a drinkable aqueous solution, in amounts up to 2.5 g of active ingredient/day, taken in several doses (up to six doses) or parenterally in the form of injectable ampoules containing up to 1 g of active ingredient (1 or 3 injections per day).

In the case of oral administration in the form of pills, capsules or tablets, these latter may advantageously contain a vehicle (such as cellulosic derivatives, vinyl polymers or gums) for modulating release of the active ingredient. The drinkable aqueous solutions will be aqueous solutions or suspensions (vehicle=water) or partially aqueous solutions or suspensions (vehicle=water+alcohol, water+glycerine or water+propylene glycol). Finally, in the case of parenteral injection, the active ingredient may be injected in the form of injectable suspensions or solutions of lyophilisates containing this active ingredient.

We claim:

1. Compounds of formula:

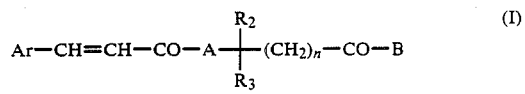

wherein:

Ar represents a phenyl nucleus; a phenyl nucleus substituted by one halogen atom, by one or three alkoxy groups with 1 to 4 carbon atoms or by one or two hydroxy groups; a 1,3-benzodioxol

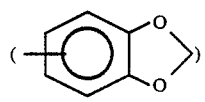

2,2-dimethyl-1,3-benzodioxol

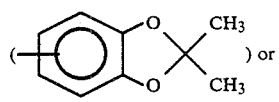

1,4-benzodioxanyl

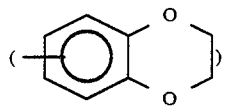

group; or a group of structure

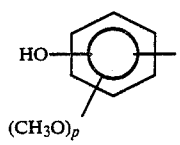

in which p is 1 or 2; CO—A— represents one of the following groups:

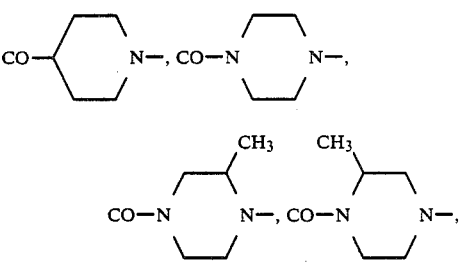

-continued

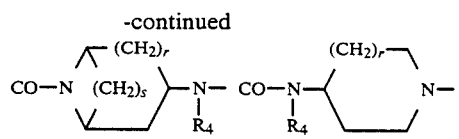

where r is 0 or 1; s is 0, 2 or 3; and $R_4$ is hydrogen or $C_1$-$C_4$ alkyl;

B represents a group chosen from the following: pyrrolidino; piperidino; morpholino; hexamethyleneimino;

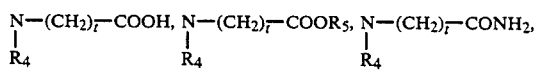

where t is 1, 2, 3 or 4, $R_4$ is hydrogen or $C_1$-$C_4$ alkyl $R_5$ is $C_1$-$C_4$ alkyl; when B is a heterocycle group, it is bonded to the adjacent CO group through the hetero cycle ring nitrogen atom;

$R_2$ and $R_3$ each represents hydrogen or $C_1$-$C_4$ alkyl, not however, repesenting simultaneously an alkyl group having more than one carbon atom; and n is 0, 1, 2 or 3; including the enantiomers and diastereoisomers forms and the trans (E) and cis (Z) forms; as well as the addition salts with organic or mineral acids or bases, the hydrates and the N-oxides of compounds (I); with the proviso that A cannot represent

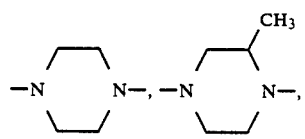

or

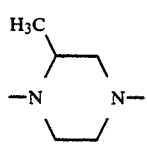

when B represents pyrrolidino, piperidino, morpholino or hexamethyleneimino.

2. The compounds as claimed in claim 1, wherein the chain —CH=CH—CO— is of trans (E) configuration.

3. The compounds as claimed in claim 2, wherein Ar is

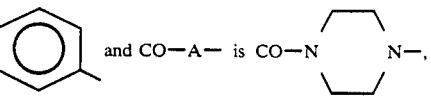

and CO—A— is

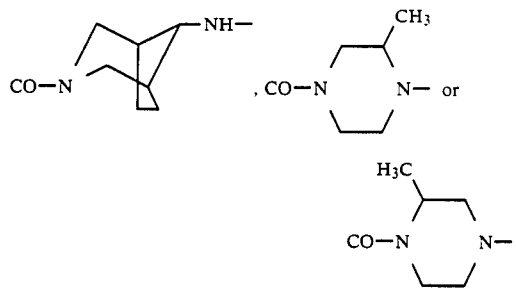

4. The compound as claimed in claim 3, of formula:

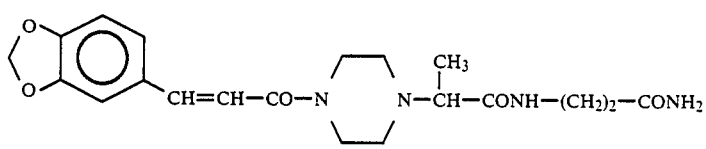

or an addition salt thereof with acid or a base.

5. The compound as claimed in claim 3, of formula:

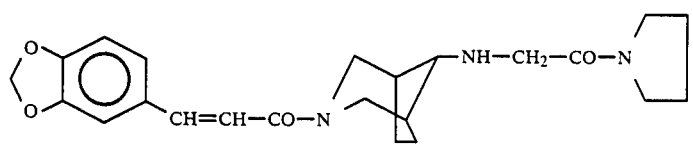

or an addition salt thereof with acid or a base.

6. A pharmaceutical composition having a memory enhancing activity, comprising a therapeutically effective amount of a compound as claimed in claim 1, with a pharmaceutically acceptable carrier.

7. A method for enhancing the memory which comprises internally administering to a patient a therapeutically effective amount of a compound of formula:

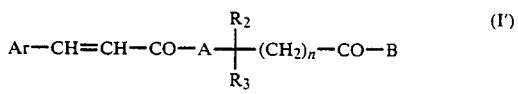

wherein:

Ar represents a phenyl nucleus; a phenyl nucleus substituted by one halogen atom, by one or three alkoxy groups with 1 to 4 carbon atoms or by one or two hydroxy groups; a 1,3-benzodioxol

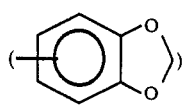

2,2-dimethyl-1,3-benzodioxol

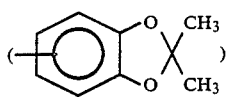

or 1,4-benzodioxanyl

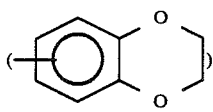

group; or a group of structure

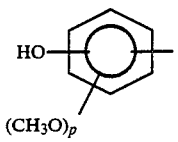

in which p is 1 or 2; CO—A— represents one of the following groups:

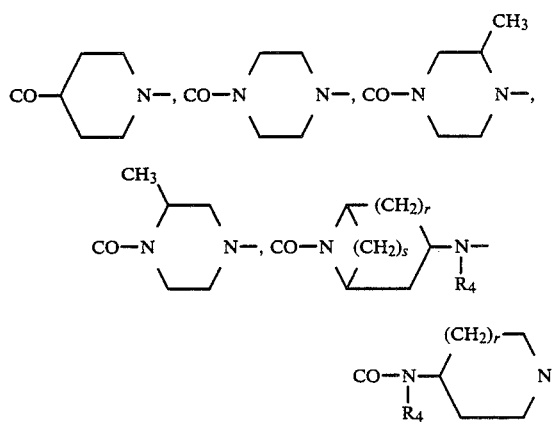

where r is 0 or 1; s is 0, 2 or 3; and $R_4$ is hydrogen or $C_1$-$C_4$ alkyl;

B represents a group chosen from the following: pyrrolidino; piperidino; morpholino; hexamethyleneimino;

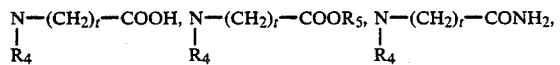

where t is 1, 2, 3 or 4, $R_4$ is hydrogen or $C_1$-$C_4$ alkyl;
$R_2$ and $R_3$ each represents hydrogen or $C_1$-$C_4$ alkyl
$R_5$ is $C_1$-$C_4$ alkyl, not however, representing simultaneously an alkyl group having more than one carbon atom; and n is 0, 1, 2 or 3; including the enantiomers and diastereoisomers forms and the trans (E) and cis (Z) forms; as well as the addition salts with organic or mineral acids or bases, the hydrates and the N-oxides of compounds (I);

B however not being able to represent:
the pyrrolidino, piperidino, morpholino or hexamethyleneimino when $R_2=R_3=H$, n=O and A=

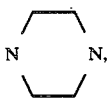

and
the pyrrolidino, piperidino, morpholino or hexamethyleneimino when Ar is 2, 3, 4-trimethoxyphenyl or 3, 4, 5-trimethoxyphenyl, the set ($R_2$, $R_3$, n)=($CH_3$, H, O), (H, H, 1), (H, H, 2) or (H, H, 3) and A=

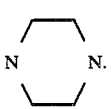

8. The method as claimed in claim 7, wherein the chain —CH═CH—CO— in formula (I') is of trans (E) configuration.

9. The method as claimed in claim 8, wherein in formula (I') Ar is

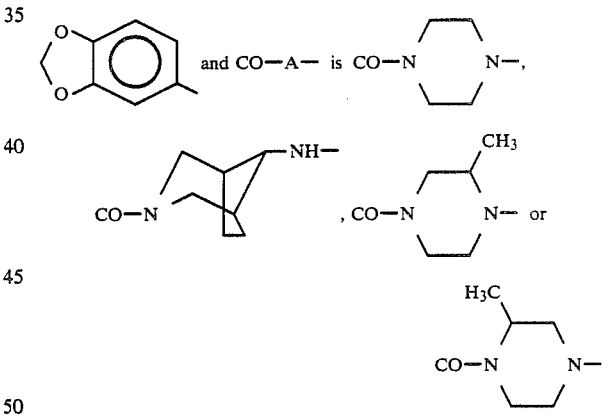

10. The method as claimed in claim 9, wherein said compound is a compound of formula:

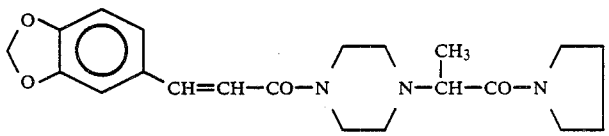

or an addition salt thereof with an acid or a base.

11. The method as claimed in claim 9, wherein said compound is a compound of formula:

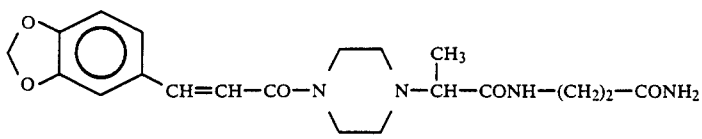

or an addition salt thereof with acid or a base.

12. The method as claimed in claim 9, wherein said compound is a compound of formula:

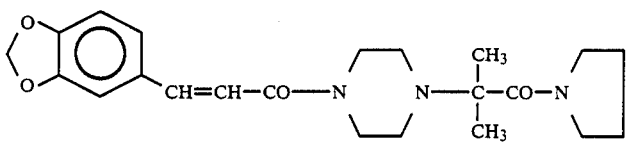

or an addition salt thereof with acid or a base.

13. The method as claimed in claim 9, wherein said compound is a compound of formula:

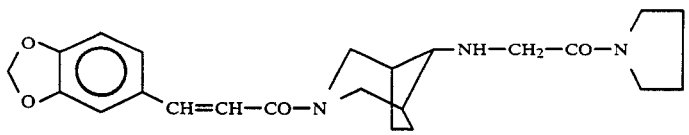

or an addition salt thereof with acid or a base.

14. The method as claimed in claim 9, wherein said compound is a compound of formula:

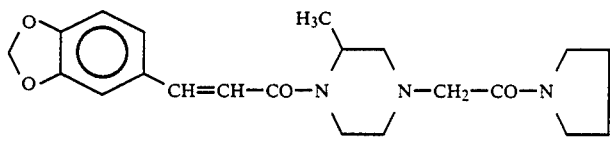

or an addition salt thereof with acid or a base.

15. The method as claimed in claim 9, wherein said compound is a compound of formula:

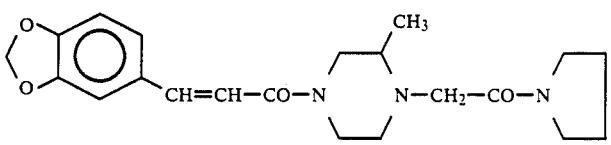

or an addition salt thereof with acid or a base.

16. The method as claimed in claim 9, wherein said compound is a compound of formula:

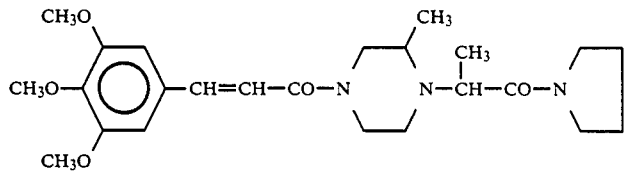

or an addition salt thereof with acid or a base.

* * * * *